United States Patent [19]
Baeuerle et al.

[11] Patent Number: 6,090,542
[45] Date of Patent: Jul. 18, 2000

[54] PROCESS FOR INHIBITING THE TRANSCRIPTION OF GENES

[75] Inventors: Patrick Baeuerle, Sasbach-Jechtingen, Germany; Thomas Henkel, San Francisco, Calif.

[73] Assignee: Boehringer Ingelheim International GmbH, Ingelheim am Rhein, Germany

[21] Appl. No.: 08/530,358

[22] PCT Filed: Mar. 31, 1994

[86] PCT No.: PCT/EP94/01014

§ 371 Date: Jan. 22, 1996

§ 102(e) Date: Jan. 22, 1996

[87] PCT Pub. No.: WO94/23045

PCT Pub. Date: Oct. 13, 1994

[30] Foreign Application Priority Data

Apr. 7, 1993 [DE] Germany .............................. 43 11 835

[51] Int. Cl.$^7$ .............................. C12Q 1/68; C12N 15/63; A61K 37/00; C07H 21/04
[52] U.S. Cl. .......................... 435/6; 435/69.1; 435/320.1; 435/325; 514/2; 536/24.1
[58] Field of Search .............................. 435/6, 69.1, 91.1, 435/240.2, 320.1, 325; 514/2; 530/200, 300; 536/24.1

[56] References Cited

U.S. PATENT DOCUMENTS

| | | | |
|---|---|---|---|
| 5,157,041 | 10/1992 | Handa et al. ............................ | 514/314 |
| 5,164,388 | 11/1992 | De et al. ................................ | 514/235 |
| 5,192,668 | 3/1993 | Treiber et al. ............................ | 435/41 |
| 5,254,682 | 10/1993 | Dhanoa et al. .......................... | 540/451 |

FOREIGN PATENT DOCUMENTS

| | | |
|---|---|---|
| 0 393 457 | 10/1990 | European Pat. Off. . |
| WO 89/08147 | 9/1989 | WIPO . |
| WO 91/01379 | 2/1991 | WIPO . |
| WO 92/14696 | 9/1992 | WIPO . |
| WO 92/20795 | 11/1992 | WIPO . |

OTHER PUBLICATIONS

Schreck et al., Dithiocarbarnates as potent inhibitors of nuclear factor kappaβ activation in intact cells, J. Exp. Medicine, vol. 175: 1181–94 (1992).

Lin et al., Cotranslational Biogenesis of NF–kB p50 by the 26S Proteasome, Cell, vol. 92: 819–828 (Mar. 20, 1998).

U.S. application No. 07/528,076, Copeland, filed May 24, 1990.

Scharpe et al., Proteases and their Inhibitors: Today and Tomorrow, Biochimie, vol. 73 (1991) pp. 121–126.

Roberts et al., Rational Design of Peptide–Based Hive Proteinase Inhibitors, Science, vol. 248 (1990), pp. 358–361.

Kempf et al., Antiviral and Pharmacokinetic Properties of C2 Symmetric Inhibitors of the Human Immunodeficiency Virus Type 1 Protease, Antimicrobial Agents and Chemotherapy, vol. 35 (1991), pp. 2209–2214.

Grimm and Baeuerle. The inducible transcription factor NF–kB: Structure–function relationship of its protein subunits. Biochem. J. vol. 290:297–308, Mar. 5, 1993.

Ten et al.. The characteization of the promoter of teh gene encoding the p50 subuit of NF–kB indicates that it participates in its own regulation. EMBO J. vol. 11(1):195–203, Apr. 3, 1992.

Ghosh and Baltimore. Activation in–vitro of NF–kB by phosphorlyation of its inhibitor IkB. Nature. vol. 344:678–682, Apr. 12, 1990.

Mark et al. Are serine proteases involved in immune complex activation of neutrophils? J. Leukocyte Biol. vol. 44:441–447, Dec. 1988.

Kantorski et al. The effect of serine and thiol protease inhibitors on the chemiluminescence of human neutrophils in investigation in vitro. J. Bioluminescence and Chemiluminescence. vol. 7:37–45, Jan. 1992.

Schreck et al. Dithiocarbamates as potent inhibitors of nuclear factor KB activation in intact cells. J. Exp. Med. vol. 175:1181–1194, May 1992.

*Primary Examiner*—George C. Elliott
*Assistant Examiner*—William Sandals
*Attorney, Agent, or Firm*—Finnegan, Henderson, Farabow, Garrett & Dunner, L.L.P.

[57] ABSTRACT

Inhibition of the transcription of genes in higher eukaryotic cells by inhibiting the activation of NF-KB, wherein the cells are treated with substances which specifically inhibit the proteolytic degradation of IKB-α directly or indirectly. Process for screening substances which inhibit NF-KB activation by inhibiting the proteolytic degradation of IKB-α. Use of the substances for treating pathological conditions which can be traced back to undesirable gene expression controlled by NF-KB.

16 Claims, 9 Drawing Sheets

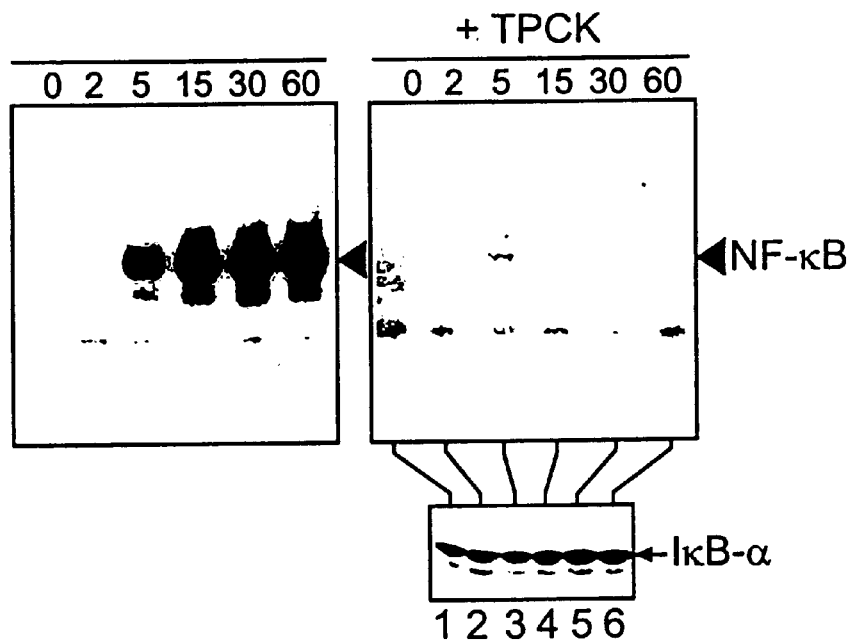
FIG. 4A
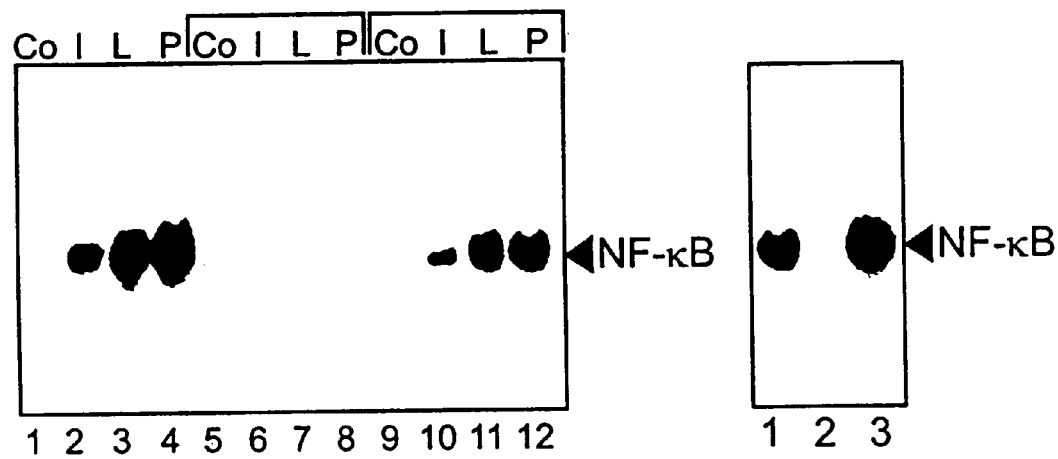
FIG. 4B
FIG. 4C

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGGRNNTYCC      10

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GGGACTTTCC      10

PROCESS FOR INHIBITING THE TRANSCRIPTION OF GENES

The invention relates to influencing the transcription of genes.

Inducible gene expression depends, amongst other things, on the inducible activation of proteins, regulating transcription by interacting with cis-regulatory DNA elements. The activity of these proteins, referred to as transcription factors, can be regulated by their de novo-synthesis; this strategy requires additional factors affecting the gene for the transcription factor. On the other hand, posttranslational mechanisms for the activation of transcription factors have the advantage of being quicker than mechanisms at the transcription level. For control of the activity of transcription factors, inhibitory protein subunits play, inter alia, an important role. An example for this is IP-1, a Leucine zipper protein, inhibiting AP-1. In this case the inhibitory subunit assumes the function of a trans-dominant negative regulator based on a structural homology with the activator. The NF-KB system is a system in which the inhibitory subunits show no homology with the DNA-binding subunits. The inhibitory subunits of NF-KB and the related factors are referred to as IkB proteins, reversibly inhibiting the binding of the transcription factor to DNA (Baeuerle and Baltimore, 1988a,b).

NF-KB, a heterodimeric factor consisting of a 50 kDa (p50) and a 65 kDa (p65) DNA-binding subunit, contributes to the so-called "immediate-early" activation of defence genes if cells are exposed to primary or secondary pathogenic stimuli (Baeuerle, 1991, Baeuerle and Baltimore, 1991).

The transcription factor NF-KB (Grimm and Baeuerle, 1993; Blank et al., 1992; Nolan and Baltimore, 1992) is, inter alia, activated by treating cells with bacteriological stimuli (inter alia LPS), viruses (inter alia HIV virus type 1), viral products, parasites, inflammatory cytokines (inter alia TNF-α, TNF-β, IL-1, IL-2), T-cell mitogens (inter alia lectines), protein synthesis inhibitors (inter alia cycloheximide), physical stress (UV-light, gamma radiation), oxidative stress (inter alia hydrogen super oxide) and tumour promoters (inter alia phorbol ester) (Baeuerle, 1991).

The activation of NF-KB in response to a large number of pathogenic stimuli is carried out by a mechanism which, as yet, has not been completely explained. Subsequent to activation, NF-KB is transferred into the cell nucleus and the target genes are activated by active NF-KB. It is assumed that reactive oxygen compounds play a role as messengers during the activation of NF-KB (Schreck et al., 1991).

It has been proven that the activation of NF-KB is connected with the release of the inhibitory subunit IkB from a cytoplasmic complex including the DNA-binding subunits p50 and Rel-A (formerly referred to as p65) (Baeuerle and Baltimore 1988 a,b). As a result of experiments with cell extracts it was assumed that the release of the inhibitory subunit IkB-α and the activation of NF-KB was due to the phosphorylation of IkB-α by protein kinase C (PKC) and other kinases (Shirakawa and Mizel, 1989; Ghosh and Baltimore, 1990; Kerr et al., 1991).

The following gene classes are controlled by NF-KB; they all contain a decameric DNA motif with the consensus sequence 5'-GGGRNNTYCC-3'(SEQ. ID. NO. 1) which is recognised by NF-KB: viral genes (HIV-1-, cytomegalo-, SV 40-, adenovirus), immune receptors (inter alia light immunoglobulin-k-chains, T-cell receptor B, adhesion molecule 1), cytokine (IFN-β, GM-CSF, IL-2, IL-6, TNF-α, TNF-β), acute phase proteins (inter alia angiotensinogen), transcription factors (inter alia "interferon regulatory factor-1", NF-KB precursor p50), vimentine. (Baeuerle, 1991).

In view of numerous pathological conditions in which the activation of the genes by the transcription factor NF-KB takes part, there is a need for NF-KB inhibitors to inhibit the transcription of genes which could have a harmful effect on the organism.

Prior art solutions suggested for inhibiting the expression of genes under the transcriptional control of NF-KB, are based on a control of the dissociation of the NF-KB/IkB-α-complex (WO 89/08147 and WO 92/20795).

The present invention has the task of explaining the mechanism of the NF-KB activation and to provide inhibitors based on this which specifically intervene in this mechanism.

Surprisingly it was found that IkB-α (previously referred to as MAD-3; Haskill et al., 1991) disappears within minutes after the stimulation of cells with phorbol ester, IL-1, LPS or TNF-α, a process coinciding with the appearance of active NF-KB. The treatment of cells with protease inhibitors or an antioxidant prevents the inducible depletion of IkB-α as well as the activation of NF-KB. Experiments carried out as part of the invention showed that the activation of NF-KB by PMA or other stimuli were obviously due to a transiently increased degradation of IkB-α by a chymotrypsin-like protease. Furthermore it was shown, that certain protease inhibitors cause the accumulation of a phosphorylated form of IkB-α. The direct phosphorylation and subsequent inactivation of IkB-α by PKC or other kinases are, however, in contrast to earlier assumptions, insufficient to activate NF-KB in intact cells.

The present invention refers to a process for inhibiting the transcription of genes in higher eukaryotic cells by inhibiting the activation of NK-KB. The process is characterised in that the cells are treated with a substance, which specifically inhibits the proteolytic degradation of IkB-α.

The inhibition of the proteolytic degradation can be direct or indirect. It is insignificant, whether the proteolytic degradation of IkB-α takes place after its dissociation from the p50/p65 complex or if IkB-α is degraded by the proteolytic degradation as part of the heterotrimeric complex.

Substances directly inhibiting the proteolytic degradation are protease inhibitors.

In the experiments an effect of serine protease inhibitors on IkB-α and the NF-KB activation was noticed. As the substances tested were toxic compounds, these compounds can not be used therapeutically. For therapeutic use substances effecting a specific inhibition of the proteolytic degradation of IkB-α by inhibiting the activation of the IkB-α protease, as specifically as possible, can be considered.

Protease inhibitors can function on the basis of their analogy with the substrate, i.e. IkB-α, by competing with IkB-α as substrate for the protease.

A further mechanism by which an inhibitor can impair the proteolytic degradation of IkB-α is by blocking the accessibility of IkB-α for the protease, e.g. by accumulating or bringing about a conformational change (allosterically effective inhibitor).

The results from the experiments carried out for the present invention show that IkB-α only becomes accessible to proteolytic degradation by being posttranslationally modified by phosphorylation.

As part of the present invention experiments were carried out with the protease inhibitor Z-Ile-Glu (OtBu)-Ala-Leucinal (hereinafter also referred to as NBIG), which is known to inhibit a component of the proteasome, having a chymotrypsin-like specificity. Experiments with regard to the influence of this inhibitor on the activation of NF-KB and the stabilisation of IkB-α have shown that it prevents the activation of NF-KB in HeLa cells after TNF stimulation, the $ID_{50}$ being of the same magnitude as the proteasome inhibition previously shown by this inhibitor. The inhibitor furthermore has the special feature that it causes an accumulation of more highly phosphorylated form of IkB-α. The occurrence and stabilisation of this phosphorylated form do not occur simultaneously with the activation of NF-KB, confirming the assumption that a phosphorylation in intact cells is insufficient for the activation of NF-KB. This indicates that the inducible phosphorylated form of IkB-α is still contained in the complex with NF-KB; the phosphorylation of IkB-α consequently does not cause a separation of IkB-α from the complex, as was initially assumed from in vitro experiments. The results achieved with NBIG show on the whole that the proteasome is responsible for the selective degradation of the phosphorylated form of IkB-α.

From the results it can be assumed, that the only function of the phosphorylation is to mark IkB-α for a subsequent rapid proteolytic degradation. The resulting lack of activity of the phosphorylated form explains why up to now no cell-free activation of NF-KB was observed.

In addition, therefore, substances indirectly inhibiting the proteolytic degradation of IkB-α by preventing the modification through which the IkB-α is changed to the form accessible to the proteolytic degradation, that is the phosphorylated form and especially substances inhibiting the kinase responsible for this, can be considered as inhibitors for the activation of NF-KB.

A further option for an indirect mechanism of protease inhibition is an inhibitor which prevents the activation of the protease, i.e. a hypothetical protease inhibitor being prevented from being released from the IkB-α protease.

The inhibitors used in the invention differ in their operation from substances inhibiting an activation of NF-KB, by inhibiting the dissociation of IkB-α from p50/Rel-A- heterodimer.

The prior suggested methods for detecting substances negatively or positively influencing the NF-KB activation were based on testing chemical substances for their ability to stabilise the complex or to promote its dissociation (WO 92/20795, WO 89/08147).

Other screening procedures are based on testing substances for their ability to modulate the transcription of a specially interesting gene, the modulation of transcription being carried out at the level of DNA binding (WO 91/01379).

The present invention has on the other hand a further purpose of offering a screening process based on knowledge gained about the mechanism of NF-KB activation, enabling the detection of substances with a high specificity for NF-KB activation, by recording substances inhibiting the proteolytic degradation of IkB-α.

A further aspect of the invention refers to a procedure for identifying substances inhibiting NF-KB activation. The procedure is characterised in that the substances are tested for their ability to specifically inhibit the proteolytic degradation of IkB-α, by a) treating an IkB-α containing substrate, in the presence of a test substance, with a preparation showing proteolytic activity for IkB-α, and determining, whether and to what extent the test substance specifically inhibits the proteolytic degradation of IkB-α, and if necessary b) and in the presence of the test substance, inducing NF-KB activation in higher eukaryotic cells, especially human cells that have been transformed with a reporter gene construct responding to the NF-KB activation and measuring the expression of the reporter gene.

In a preferred embodiment of the process purified IkB-α is used in a so-called "cell-free" assay as the substrate of step a).

This can for instance be carried out by binding a defined quantity of preferably recombinant IkB-α (Henkel et al., 1992; Zabel et al. 1993), marked so as to be measurable, to a fixed carrier.

A preparation showing proteolytic activity for IkB-α is applied to the immobilised IkB-α in presence of the test substance. This preparation could either be a so-called "activated" cell extract or IkB-α protease produced by a recombinant method, as soon as it is available. If the assumption is correct, that the IkB-α protease is a component of the proteasome (Orlowski, 1990; Rivett, 1989), this can be used in a purified form or a part thereof as the proteolytic activity.

An activated cell extract showing IkB-α degradation activity is obtained from cells which were treated with a known NF-KB inducer such as LPS, phorbol ester, TNF, etc. The induction of NF-KB activity effects an activation of the system responsible for the proteolytic degradation of IkB-α. The cell extract preferably contains no IkB-α degrading activity in its non-activated state.

The activated cell extract can be used to detect direct and indirect inhibitors of the proteolytic IkB-α degradation. If using purified IkB-α protease, only inhibitors acting directly on the protease are registered.

As a preparation with proteolytic activity for IkB-α, a preparation of induced cells may furthermore be used in cell-free assays, being preferably a fraction of the activated cell extract in which IkB-α proteolytic activity was proven. The protein chemical methods for fractionating the cell extracts are known to experts. The fractions obtained for instance after ammonium sulphate precipitation, gel filtration and/or ion exchange chromatography, isoelectric focusing, etc., are tested in pretrials for their ability to proteolytically degrade IkB-α and the respective fraction is used for the assay, the quantity being coordinated with the test substrate IkB-α in such a way that the degradation can be measured.

In the absence of a test substance (control), or with a test substance not having an inhibiting effect on the proteolytic activity, the immobilised IkB-α is proteolytically degraded. This is shown by the fact, that the marked form of IkB-α (e.g. a radioactive or a fluorescent marker) passes completely or in part (during complete or partial degradation of IkB-α) from the carrier to the supernatant. The proportion of the marker having changed from the carrier to the supernatant is proportional to the proteolytic degradation of IkB-α. In the presence of a test substance, inhibiting the proteolytic degradation of IkB-α, the immobilised IkB-α is not degraded, the marking remains on the carrier and none passes to the supernatant.

Alternatively a stipulated quantity of marked IkB-α may be present in soluble form instead of being immobilised on a carrier during step a), whilst the other test parameters are identical to the above test arrangement. When applying a preparation with proteolytic activity the IkB-α of the solution is broken down into smaller species. The components of the solution are then separated, e.g. by dialysis or gel filtration, the pore size of the membrane or of the resin being chosen so that the intact IkB-α is separated from the proteolytic fragments. The marked fragments or the non-degraded marked IkB-α substrate are now in the eluate, with the fraction of the fragments to the total being proportional to the proteolytic degradation of IkB-α. In the presence of a test substance inhibiting the proteolytic activity, the IkB-α contained in the solution is not degraded and consequently no marked fragments can be detected.

A further alternative for a cell-free assay in step a) is the generation of a IkB-α complex with p50 and/or p65, the components being preferably of recombinant origin, as soon as this is completely available, and IkB-α having a measurable marker to treat this complex in the presence of the test substance with a preparation having proteolytic activity. If proteolysis occurs, which is the case if the test substance is not able to inhibit this activity, the IkB-α is digested by the complex and the marker is on the proteolytic fragments which after filtration will, in this case too, be detectable in the eluate. In case of an inhibitory effect of the test substance on the proteolytic activity, IkB-α remains associated with the complex and no marker passes into the eluate. In principle the proteolytic degradation of IkB-α can also be observed with the change of the fluorescence of the complex, depending on the structural change.

The findings of the present invention, that the protease inhibitor NBIG effects the accumulation of a phosphorylated form of IkB-α, enables a variant cell-free assay in which the phosphorylated form of IkB-α can be used as substrate for the protease. After having initially tested by Western blotting with IkB-α antibodies or ELISA with the addition of proteases, e.g. the purified proteasome or protease containing cell fractions, whether phosphorylated IkB-α is indeed the form of the substrate inactivated by a protease (constitutive) for the degradation, this substrate can be generated as follows:

Suitable human cells, expressing NF-KB and IkB-α, i.e. HeLa cells or 293 cells (ATCC CRL 1573), are treated with a protease inhibitor, which caused in pretrials an accumulation of a phosphorylated form of IkB-α, for instance with NBIG at a concentration of 75 $\mu$m. The cells are then stimulated with an inducer of NF-KB activation for a period required for this activation, i.e. with TNF-A for 15 minutes, or with PMA or IL-1. The NF-KB-IkB-α complex from cytoplasmatic extracts of treated cells containing IkB-α in phosphorylated form, is accumulated, if necessary, for example by a glycerine gradient, gel filtration or ion exchange chromatography, and is separated from surplus NBIG and from this inactive endogenous protease. To transform IkB-α completely into the phosphorylated form, preferably a phosphatase inhibitor such as okadaic acid is added in a suitable concentration, e.g. 100 nmol.

The phosphorylate IkB-α thus obtained, being the substrate for the protease and leading to the activation of NF-KB, may be used in the above assays for finding inhibitors of the activation of NF-KB (alternatively IkB-α may be provided in phosphorylated form, by phosphorylating recombinant IkB-α in vitro. The principle of the assay remains the same: without protease inhibitors (without the addition of test substances or in the presence of test substances having no inhibitory effects) the phosphorylated substrate is degraded. In the presence of the inhibitors the phosphorylated form of the NF-KB-IkB-α complex remains detectable.

To narrow down the positive results of step a) with regards to the specificity of the test substances for the proteolytic degradation of IkB-α, additional controls are required:

An inhibitor found for instance in step a) is tested to determine whether it affects the activity of other proteases. This is done in such a way that the effect of the inhibitor on the activity of the protease having a different substrate to the IkB-α is analysed.

To establish whether the inhibitor reacts indirectly, that is on the IkB-α substrate, the effect of the inhibitor with a known protease is tested, e.g. chymotrypsin (pretrials must have established that the inhibitor does not directly influence the activities of this control protease).

The results obtained from the present invention suggest that the IkB-α protease is a chymotrypsin-like serine protease. After confirmation of these findings in the cell-free system by the inhibitor TPCK, the screening procedure of the invention can be extended by testing the main derivatives of serine protease inhibitors. As a control, the effect of the established inhibitor on the serine protease, e.g. chymotrypsin on one hand and on the IkB-α protease on the other, is tested. (In case that, contrary to expectations, these findings are not confirmed, one can proceed analogously by testing the main derivatives of inhibitors of the protease class to which the IkB-α protease is definitely assignable, and implementing the respective controls.)

The selection of the most suitable assay variations is made through pretrials, e.g. whether IkB-α on its own, or in a phosphorylated form or in association with its complex partners p50 and/or p65 serves as test substrates as well as the specific assay conditions.

The other assay conditions, such as the method and concentration of the inducer, duration and condition of the induction, cell disintegration, IkB-α quantity or that of possibly present complex partners, carriers and binders of IkB-α or of the complex partners to the carrier (binding to microtiter plates using a bivalent cross linker such as glutardialdehyde, to sepharose via cyanogen bromide, etc.), markers (coupled enzyme, radioisotope, fluorescent, chemiluminescent or bioluminescent substances, etc.), period of treatment, arrangement and number of controls, etc. are optimised via pretrials.

The assay conditions in step a) are preferably chosen so that the assay can be automated.

In the case that the specificity of the inhibitor within the assay carried out using the cell extract was not completely clear with regards to the inhibition of the IkB-α protease, a so-called cellular assay (step b) is carried out after the cell-free assay or parallel to it, in which the effect of the test substance on the activation of NF-KB in the intact cell is established. Step b) is preferably carried out in any case to confirm an inhibitory effect of the test substance in an intact cell found in the cell-free assay.

The reporter gene construct with which the test cell used in b) is transformed, is hereinafter referred to as "sensor-DNA". This refers to a DNA construct containing a reporter gene being controlled by regulatory sequences and responding to the activation of NF-KB by containing at least one binding sequence for NF-KB. During activation of NF-KB, NF-KB binds to the recognition sequence after which the expression of the reporter gene is initiated, giving a measurable signal.

The sensor DNA is preferably located on a plasmid which is highly reproducible in a suitable host organism, preferably *E. coli* and facilitates the expression of a reporter gene under the control of regulatory elements after transfection into mammalian cells and integration into the host genome. For this preferably a shuttle vector is chosen containing an expression cassette for the reporter gene (sensor DNA) and a selectable marker for mammalian cells as well as at least one replication origin and a marker for the selection in *E. coli*.

To produce permanent cell lines containing stable sensor DNA integrated into their genome, the vector contains a dominant selection marker. The use of a specific selection marker is non-critical, for which, for instance, the gene for neomycin-phosphotransferase (neo), offering resistance against antibiotic geneticin (G-418) (Southern and Berg, 1982) the DHFR gene (Dihydrofolatreductase) for DHF-deficient cells, the gene for xanthine-guanine-phosphoribosyltransferase (gpt), offering resistance against mycophenolic acid (Mulligan and Berg, 1981) or the hygromycin-B-phosphotransferase gene (hph; Gritz and Davies, 1983) are suitable. Examples of promoters driving the selection marker gene are the SV40 early promoter, the cytomegalovirus promoter (CMV promoter), the promoter of the thymidine kinase gene of the herpes simplex virus (TK promoter), the Rous sarcoma virus (RSV) long terminal repeat (LTR). The plasmids are preferably constructed in such a way that individual important elements such as the reporter gene, the promoter for the reporter gene or the regulatory sequences for the selection marker can be exchanged or changed to correspond to possible changed requirements resulting from the particular application, e.g. due to the use of a different cell line. Such measures would be for instance to install multi-cloning sites before the promoter(s) or the reporter gene to facilitate the cloning of regulatory sequences, modulating the promoter, from various reporter genes.

When selecting a suitable reporter gene it is assumed that preferably a non-radioactive, automatable assay of high sensitivity is provided.

In principal all reporter genes fulfilling these preconditions can be used for the present invention:

Alkaline phosphatase can be measured if using a chemiluminescent substrate with high sensitivity, although it has the disadvantage that this enzyme is relatively strongly expressed by many mammalian cells. It is consequently only suited for cell lines which do not express it or express it only to a limited extent.

The expression products of the β-galactosidase and the β-glucuronidase gene can cleave the respective methylumbeliferyl-galactoside or glucuronide whilst forming fluorescent groups. These enzyme reactions are observed by using established fluorescent assays (Wieland et al., 1985; Kricka, 1988).

Expression of chloramphenicol actetyltransferase (CAT) can be detected with relative sensitivity, the assay has, however, inter alia the disadvantage that it is radioactive and difficult to automate (Hartmann, 1991).

Within the context of the present invention the gene encoding Photinus pyralis-luciferase (De Wet et al., 1987) is used as a reporter gene. This enzyme has the advantage that together with its substrate luciferone it generates a high level of bioluminescence when ATP is added, which can be measured with established, automatable methods, and that this enzyme is not produced endogenously by mammalian cells. Luciferase also has a relative short in vivo half-life and is non-toxic even in high concentration (Hartmann, 1991; Brasier et al., 1989). The measurement of the activity of firefly luciferase using bioluminescence is one of the most sensitive methods for detecting enzymes. Consequently, and due to the absence of luciferase activity in normal mammalian cells, this enzyme is especially suitable as a reporter gene (Subramani and DeLuca, 1987).

Alternatively the gene coding for the enzyme apoaequorine of the jellyfish aequoria victoria (Tanahashi et al., 1990) can be used as reporter gene. This enzyme has the advantage that it generates large amounts of bioluminescence together with its co-factor coelenterazine after binding calcium ions, which can be measured with established automatable methods. Another advantage is, that this enzyme is not endogenously expressed by mammalian cells.

The reporter gene is driven by a promoter, which is independent of other factors and makes the induction of gene expression clearly visible, e.g. the thymidine kinase promoter. The promoter must transcribe the reporter gene it drives in a correct and measurable way. Minimal promoters, for instance the minimal TK-promoter and the minimal-β-globin promoter, are available. For the cellular assays carried out as part of this invention, the −105−+52 TK promoter was used, having a relatively high basal activity and being easily stimulated; in pre-trials the −30 and the −87 minimal-TK promoters were also proven to be suitable.

In principle any of the consensus sequences 5'-GGGRNNTYCC-3' (SEQ. ID. NO. 1) are suitable as binding motifs for NF-KB, e.g. the well characterised motif of the light immunglobulin K-chain, having the sequence (SEQ. ID. NO. 2) may be used. The NF-KB binding motif appears for this purpose at least twice within a short distance (approx. 10 nucleotides). For the experiments six KB motifs were used.

In principle NF-KB binding sequences can be used from any gene which is controlled by NF-KB. (Baeuerle, 1991). If the genes also contain binding domains for other transcription factors, apart from the NF-KB binding sequence, these are preferably removed.

Control cells are preferably cells containing no DNA binding motif for NF-KB in their reporter gene. The control cells facilitate the detection of a non-specific effect of the substance on gene expression; for instance, a signal contained in the control cell would originate from baseline transcription and should therefore be deducted from the signal contained in the test cell.

The test cells must fulfill the condition that endogenous NF-KB can easily be activated inside them. NF-KB should not be constitutive in these cells.

The cells should also be induciable with substances activating NF-KB, such as PMA, LPS, $H_2O_2$, UV.

Cells can be tested for their suitability as test cells by transforming them with the sensor DNA; and the kinetics of induction of reporter gene expression determining the concentration dependence of the cell inductor.

For an automatic process the cells should be as adherent as possible.

In the procedure according to the invention, substances directly or indirectly inhibiting the proteolytic degradation of IkB-α and thus the activation of NF-KB are detected, as well as substances inhibiting the phosphorylation of IkB-α. It is insignificant for the inhibitory effect, whether the protease itself is specific to IkB-α, essential is the specificity with regard to the activation. In a further aspect, the invention relates to substances which specifically inhibit the proteolytic degradation of IkB-α, for the treatment of pathological conditions, to which expression of genes controlled by the transcription factor NF-KB contribute.

Pathological conditions caused by an adverse effect of gene expression by NF-KB activation include, inter alia, inflammatory illnesses resulting from an activation of T cells, macrophages or B cells, toxic shock, illness after infection by a virus containing the KB motif, UV-damage (sunburn), radiation damage, burns, transplant rejection, reperfusion damage.

For therapeutic use, substances identified according to the procedure of the invention are formulated, which are then characterised in more detail for the development of medication in the usual way with regard to their pharmacological characteristics, e.g. in secondary screening and animal tests, depending on the delivery with suitable pharmaceutically acceptable carrier and auxiliary substances, guaranteeing the bioavailability of therapeutically effective substances and not having damaging effects on the organism. Methods for the formulation of pharmaceutic preparations can be found in standard text books, e.g. Remington's Pharmaceutical Sciences, 1980.

As part of the present invention, the effect of protease inhibitors on the proteolytic degradation of IkB-α was determined. The inhibition of NF-KB activation in induced test cells containing an NF-KB-responsive luciferase gene construct was confirmed, as well as inhibition of the NF-KB regulated expression of IL-6 and IL-8. As part of the present invention the fate of the NF-KB specific inhibitory subunit IkB-α was observed after the treatment of cells with NF-KB activating stimuli. For this purpose, highly purified recombinant human IkB-α was used to generate a rabbit antiserum; specific IgG was affinity-purified by immobilised IkB-α. The IkB-α specific polyclonal IgG recognised a single 38 K band at the correct size for IkB-α (FIG. 1A, lane 1) in Western blots in a total cell extract of mouse 7OZ/3 pre-B cells. This band was not recognised by a control antibody (anti-rabbit IgG antibody) (FIG. 1A, lane 2). Between 2 and 5 minutes after the addition of phorbol-12-myristyl-13-acetate (PMA) to the 7OZ/3 cell cultures the IkB-α band disappeared almost completely from the cells (FIG. 1B, compare lanes 3 and 4). The cells then showed no IkB-α immunoreactivity until 40 minutes after stimulation (FIG. 1B, lane 7). Aliquots of the same cell extract were analysed using the Electropheric Mobility Shift Assay (EMSA) for KB-specific DNA binding activities. As apparent from FIG. 1C (compare lanes 2 and 3), the disappearance of IkB-α coincided exactly with the appearance of the NF-KB-DNA binding activity, suggesting a causal relationship between these two events.

NF-KB may also be activated in 7OZ/3 cells by treatment with IL-1β and LPS. The activation of NF-KB by TNF-α can be studied in HeLa cells. As shown in FIG. 2, IL-1β, LPS and TNF-α all induced a decay of IkB-α in 7OZ/3 or HeLa cells. There were, however, no kinetic differences with regard to the start of the disappearance of IkB-α. Most of the IkB-α had already decayed 5 minutes after stimulation of the 7OZ/3 cells with PMA (FIG. 1B) or of the HeLa cells with TNF-α (FIG. 2). When stimulating the 7OZ/3 cells with IL-1B, the decay started somewhat later; after 5 minutes of stimulation more IkB-α remained than had been observed in the cells treated with PMA or TNF-α (FIG. 2B). In 7OZ/3 cells stimulated by LPS most of the IkB-α was not degraded before 30 minutes from the induction (FIG. 2).

Again and for all three inducers, the disappearance of IkB-α coincided with the appearance of NF-KB-DNA binding activities in the cells. These observations show that four different inducers of NF-KB use a mutual mechanism of NF-KB inactivation, contributing to a decay of IkB-α. The varying kinetics of the degradation suggests that the inducers use different signal transduction paths before NF-KB activation. Based on the fact that a polyclonal antibody was used, it is unlikely that only an epitope of IkB-α was lost or modified after the stimulation. It is more likely that the loss of IkB-α immunoreactivity is due to a rapid and complete decay of the protein leading to no immunologically detectable degradation product. After stimulation with PMA, IL-LB, LPS or TNF-α, no change of the electrophoretic mobility of IkB-α in SDS gels was visible, indicating a posttranslational modification of IkB-α before this degradation.

It is known that the protein synthesis inhibitors cycloheximide and anisomycin, activate NF-KB in 7OZ/3 cells (Sen and Baltimore, 1986). The one-hour treatment of 7OZ/3 cells with cycloheximide carried out within the context of this invention induced only slightly the binding of NF-KB to DNA (FIG. 3A, lane 1, top panel). In these cells large amounts of IkB-α could still be detected by Western blotting (FIG. 3A, lane 1, lower panel). This leads to the conclusion that the inhibition of the normal IkB-α transformation is insufficient for an efficient and rapid activation of NF-KB. If cells pre-treated with cycloheximide were induced with PMA a rapid decay of IkB-α and consequently an induction of the binding of NF-KB to DNA may be observed (FIG. 3A); the early kinetics of the established IkB-α reduction could not be differentiated from those observed with PMA alone (compare FIG. 3A with FIG. 1B). The protein synthesise inhibitor cyclo-heximide prevents, however, the reoccurrence of IkB-α, which was observed 40 minutes after the treatment with only PMA (compare FIG. 3A with FIG. 1B), suggesting that this IkB-α was newly synthesised, possibly under transcriptional control of NF-KB itself.

Furthermore, the half-life of IkB-α in protein synthesis arrested cells was determined without or with subsequent PMA stimulation of the cells. The half-life of IkB-α in cycloheximide-treated 7OZ/3 cells was approx. 138 minutes, as analysed by quantitative Western blotting (FIG. 3B). The half-life of IkB-α was reduced to only 1.5 minutes during the period of its most rapid degradation, 2 to 5 minutes after the PMA stimulation; this shows that PMA induces an approx. 90-fold degradation of IkB-α.

To determine whether the inducible degradation of IkB-α is a necessary step for the activation of NF-KB, cell cultures were treated with protease inhibitors. Of the various substances found to be active, the chymotrypsin inhibitor p-tosyl-L-phenylalaninechloromethylketone (TPCK) was the most potent inhibitor of NF-KB activation in the various cell types. A one-hour treatment of 7OZ/3 cells with 25 $\mu$M TPCK was sufficient to completely suppress the NF-KB-DNA binding activity in a subsequent PMA treatment (FIG. 4, top panel). The ID50 of TPCK was approx. 8 $\mu$M. The constitutive DNA binding activity, including nuclear-factor oct-1, was not significantly influenced (FIG. 4A). As shown by the Western blot, the protease inhibitor was able to completely prevent the degradation of IkB-α in PMA treated cells (FIG. 4A, lower panel). TPCK had an inhibitory effect even when added simultaneously with the PMA and was at the same time effective in preventing the activation of NF-KB by IL-IB and LPS in 7OZ/3 cells (FIG. 4A, lanes 6 and 7) and with TNF-α in various other cell lines. The treatment of cells with the protease inhibitor after stimulation with PMA, IL-1 or LPS hardly impaired the NF-KB activation, but should, however, have stopped further activation (FIG. 4A, lanes 10–12). This shows that TPCK did not just simply impair the DNA binding of NF-KB or lead to the degradation of NF-KB, processes which had occurred during the cell lysis. It is equally unlikely that TPCK inhibited PKC, as IL-1B and TNF-α were shown to activate NF-KB independently from PMA-induciable PKC isoenzymes (Bomsztyk et al., 1991; Meichle et al., 1990).

p-tosyl-L-lysinchloromethylketone (TLCK) is an inhibitor of trypsin-like serine proteases and is quite similar to TPCK in structure and chemical activity. TLCK was unable to prevent the activation of NF-KB in 7Z/3 cells at a concentration of 25 $\mu$M (FIG. 4B, lane 3). At a concentration of 100 $\mu$M TLCK, however, a partial inhibition of the NF-KB activation was observed. Various other protease inhibitors were effective, albeit at higher concentrations. The selective and strong inhibitory effect of TPCK suggests that a chymotrypsin-like serine protease is part of the NF-KB activation. This protease is hereinafter referred to as IkB-α protease.

Recently, it was reported that reactive oxygen compounds could play a role as messenger substances in the activation of NF-KB through many inducible factors (Schreck et al., 1991; Schreck et al., 1992 a,b). This assumption was partially based on the fact that antioxidants such as thiol compounds, dithiocarbamate and chelating agents for free iron, suppress the activities of NF-KB in intact cells. A very strong antioxidant inhibitor of the NF-KB activation was pyrrolidindithiocarbamate (PDTC; Schreck et al., 1992b) If the degradation of IkB-α plays a significant part in the activation of NF-KB, PDTC should, similarly to TPCK, prevent the disappearance of IkB-α, although this inhibition could operate due to a mechanism operating prior to the IkB-α protease. 100 μM of PDTC effectively suppressed the activation of NF-KB binding activities in PMA treated 7OZ/3 cells (FIG. 5). As expected no significant degradation of IkB-α protein was shown by the Western blot. Recently it was shown that PDTC does not interfere with the PMA induced membrane association and the kinase activity of PKC, arguing against a direct effect of PKC on IkB-α in intact cells.

From the results of the present invention it can be concluded that the proteolytic degradation of IkB-α in response to PMA, IL-1β, LPS and TNF-α is a necessary step in the process of NF-KB activation. This is not only apparent from the near simultaneous coupling of IkB-α degradation with the NF-KB activation, but also and more importantly from the selective inhibitory effect observed at low concentrations of the well characterised protease inhibitor TPCK. The inducible degradation was caused by a dramatic reduction in stability of the protein and not by blocking de novo synthesis. The normal half-life of the inhibitory subunit could explain the weak activation of NF-KB by protein synthesis inhibitors, but this is definitely insufficient to induce a rapid and complete depletion of IkB-α and to potently activate NF-KB as shown by PMA and other stimuli.

An increased degradation of IkB could be controlled by various mechanisms: Firstly, a new modification of the IkB protein could make the inhibitor more susceptible to a degradation by a constitutive protease. Secondly a protease selectively breaking down IkB could be activated. An interesting aspect of this possibility is that the IkB-α protease or a protease inhibitor can be a direct upstream target for messenger substances such as protein kinases. Thirdly a modification of IkB or an induction of protease activity could be required. The results available to date cannot decisively differentiate between these possibilities.

The present invention also raises the question, to what extent direct phosphorylation of IkB contributes to the release of IkB and the activation of NF-KB in intact cells. Based on the investigations carried out so far, no phosphorylation data from intact cells is available, suggesting an induciable phosphorylation of IkB-α, although a constitutive phosphorylation of IkB-α was observed. The present results only agree with the in vitro phosphorylation data (Shirakawa and Mizel, 1989; Ghosh and Baltimore, 1990; Kerr et al., 1991) under the assumption that degradation is required to quickly eliminate the IkB released by the phosphorylation. Degradation could be required to prevent IkB, once dephosphorylated, from inhibiting new NF-KB. In view of the strong inhibitory effect of the protease inhibitor TPCK, however, phosphorylation of IkB-α should be too transient to activate NF-KB and to permit its transport into the cell nucleus or to be detected by the usual methods.

A controlled proteolytic degradation of IkB would be an excellent mechanism to make the activation of NF-KB irreversible. The only option to inhibit activated NF-KB would in this case be newly synthesised IkB. An important question is whether the IkB-α protease attacks IkB-α in the cytoplasmatic complex with NF-KB, or whether a prior release of IkB from NF-KB is required. Experiments have shown that overexpressed IkB-α is not significantly degraded by a TNF-α stimulation, which, however, is the case with the endogenous version. This suggests that only the IkB associated with NF-KB is a substrate for the IkB-α protease making the requirement of identification, but not modification of IkB-α by a direct phosphorylation, obsolete. A specific structure for a subunit of a transcription regulator has already been established for the α2 repressor from yeast (Hochstrasser and Varshavsky, 1990).

Specific inhibitors of the IkB-α protease are suitable as pharmaceutical agents for preventing the activation of NF-KB, which is responsible for various pathological conditions. Examples of the numerous biomedically important conditions to which NF-KB contributes significantly as signal transferrer and activator of immediate-early genes, are the progression of AIDS, the activation of T-cells, B-cells and macrophages during the immune response, the so-called acute phase response, toxic shock, transplant rejection and the response of the cell to gamma radiation and UV light. Specific inhibitors of the IkB-α protease are effective as anti-inflammatory and immune suppressive drugs.

BRIEF DESCRIPTION OF THE DRAWINGS

FIG. 4A shows the effect of TPCK on the induction of NF-KB by PMA.

FIG. 4B shows the effect of TPCK on the activation of NF-KB by IL-1β.

FIG. 4C shows the effect of TLCK on the activation of NF-KB by PMA.

EXAMPLE 1

Figure 1A:
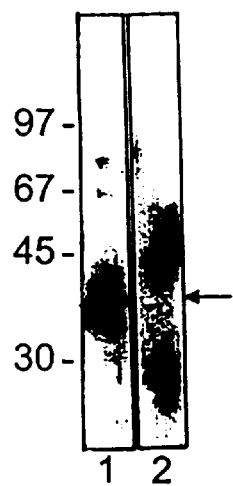
FIG. 1A is a Western blot showing the specificity of an affinity-purified polyclonal rabbit-anti IkB-α.

Fate of IkB-α in stimulated 7OZ/3 pre-B cells

7OZ/3 cells (ATCC No. TIB 158) were cultivated in RPMI-1640 medium (Gibco BRL), supplemented by 10% FCS (Gibco BRL) and 50 μM 2-mercaptoethanol. 2 ml aliquots with approx. 2–3×10$^6$ of suspended cells was treated with 50 ng/ml PMA (Sigma) for various periods. The treatment was interrupted by immediate centrifugation (5 s in an Eppendorf Microfuge) and cooling on ice. The cell pellets were lysed with 60 μl of a high-salt extraction buffer, containing the non-ionic detergent nonidet P-40 (Baeuerle and Baltimore, 1988b). The supernatant of a 15 minute centrifugation at 13.000 rpm in an Eppendorf Microfuge was analysed by Western blotting and EMSA (electrophoretic mobility shift assay). For SDS-PAGE and Western blotting 30 μl aliquots of the extracts were mixed with 15 μl SDS sample buffer (Laemmli, 1970), boiled and subjected to a SDS-PAGE on 12.5% polyacrylamide mini-gels (Biorad). The proteins were transferred by using a so-called semi-dry blotting device (Biorad; 1 h at 15V/2.5 mA/cm2) from the gels onto IMMOBILON-P-filter (0.45 μm; Millipore). The efficiency of the blot was checked by protein staining of the filters with Ponceau S (Serva). The filters were blocked overnight in a Tris-buffered saline solution, containing 0,1% (v/v) TWEEN-20 (TBST), 5% low-fat milk powder (Nestle) and 1% BSA. The filter was then incubated for one hour at ambient temperature with anti IkB-α IgG in a dialysed eluate of the IkB-α affinity column and diluted by 1:100 in the blocking buffer. After washing for 30 minutes in TBST the filter was incubated in a 1:4000 solution of goat-anti-rabbit IgG/horseradish-peroxidase conjugate (Biorad) in blocking buffer. After washing for 30 minutes in TBST the filter was treated with ECL detecting reagent (Amersham) and exposed (Kodak XR film, less than 1 minute). For EMSA 2 μl aliquots of the extracts were added to a binding mixture, resulting in a final concentration of 100 nM KCl, 20 nM HEPES, pH 7.9, 2.5 nM dithiothreitol, 0.5 nM phenylmethylsulfonylfluoride (PMSF), 0.2% NONIDET P-40, 5% FICOLL, 20 μg BSA, 3 μg Poly (dl–dC) and 10.000 cpm (Cerenkov counting method) of a $^{32}$P marked double-stranded KB-oligonucleotide probe (Gibco BRL). The specificity of the protein DNA complex was confirmed by competition experiments and supershifting with a polyclonal antibody, recognising the C-terminal 100 amino acids of Rel-A (p65). After 20 minutes of incubation on ice the samples were subjected to electrophoresis on native 4% polyacrylamide gels, run in 0.5× TBE. The dried gels were exposed (Kodak XR film, −70° C., overnight).

Human IkB-α was produced in *E. coli* and purified, as described by Zabel et al., 1993. An antiserum against IkB-α was produced in rabbits, the specific IgG in 2 ml serum, affinity purified to IkB-α SEPHAROSE (Henkel et al., 1992). 2 mg of 6× His-marked, affinity-purified human IkB-α were coupled to 0.5 ml cyanogen bromide activated SEPHAROSE 4CL-B (Pharmacia) according to the manufacturer's instructions. After thorough washing with PBS and 2 column volumes 0.1 M glycine-HCl, pH 2.7, specific antibodies were eluated with 2 volumes 4 M guanidinhydrochloride. The eluate was dialysed thoroughly with TBST.

Figure 1B:
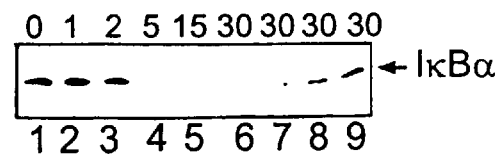
FIG. 1B shows the effect of IkB-α of a treatment with PMA.
Figure 1C:
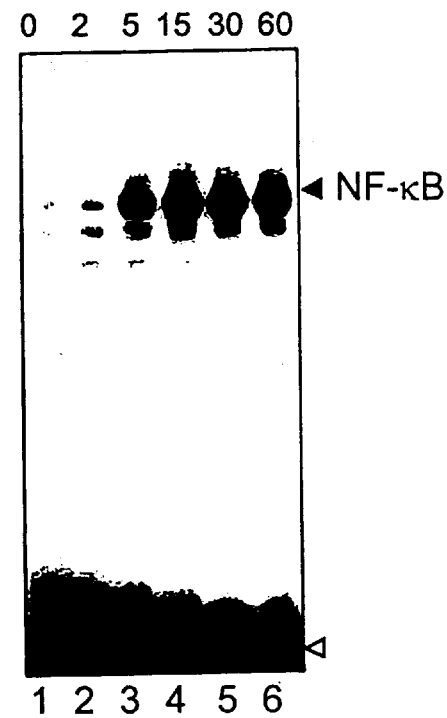
FIG. 1C shows the effect on the DNA binding activity of NF-KB of a treatment of cells with PMA.

The results of the experiments are listed in FIG. 1. A: Specificity of an affinity-purified polyclonal rabbit-anti-IkB-α antibody in Western blots. As stated above, the proteins were separated by non-stimulated 7OZ/3 cells in a high-salt total cell extract by sodium dodecylsulphate-polyacrylamide gel electrophoresis (SDS-PAGE) and transferred to a membrane filter. A strip of the filter was incubated with anti-IkB-α and a peroxidase labelled anti-rabbit IgG (lane 1). A duplicate filter was incubated on its own with the second antibody (lane 2). The figure shows the fluorograms of the chemiluminescence marked filter. The molecular weights are stated in kDa. The arrow shows the position of a single 38 K-band. Phosphorylase (97), bovine serum albumin (BSA, 67), ovalbumin (45) and carboanhydrase (30) were used as molecular weight standards. B: Effect of a treatment of cells with PMA on IkB-α. The cells were treated with PMA for the period stated in the figure (in minutes) (lanes 2–9). The zero value (lane 1) stems from untreated cells. After treatment the cell extracts were subjected as stated to a SDS-PAGE and were Western blot tested for IkB-α by using anti-IkB-α IgG. The arrow indicates the position of IkB-α. The figure shows an extract of a fluorogram. C: Effect of a treatment of cells with PMA on the DNA binding activity of NF-KB. Aliquots of extracts from control cells (lane 1) and PMA treated cells (lanes 2–6; the treatment period is stated at the top in minutes; the number underneath the figure shows the lane) were incubated, as stated, with the $^{32}$P-marked DNA-probe containing the NF-KB binding motif of the enhancer of the gene "mouse k light chain enhancer"; (Sen and Baltimore, 1986) after which an analysis of the DNA binding activity was carried out by using gel electrophoresis. The figure shows a fluorogram of a native gel. The filled arrowhead shows the portion of the NF-KB-DNA complex, the open arrowhead the position of the non-complexed DNA probe.

EXAMPLE 2

Effect of IL-1β, LPS and TNF-α on the activation of NF-KB and the stability of IkB-α

The methods used in this example for the culture of the 7OZ/3 cells and the production of the cell extracts were implemented as stated in example 1. The 7OZ/3 cells were treated with 50 E/ml IL-1β (Boehringer Mannheim) or with 15 μg/ml LPS (Sigma). Human HeLa cells were cultivated in DMEM, supplemented with 10%FCS and 1% L-glutamine and treated with 200 E/ml human recombinant TFN-α (genzyme).

Figure 2:
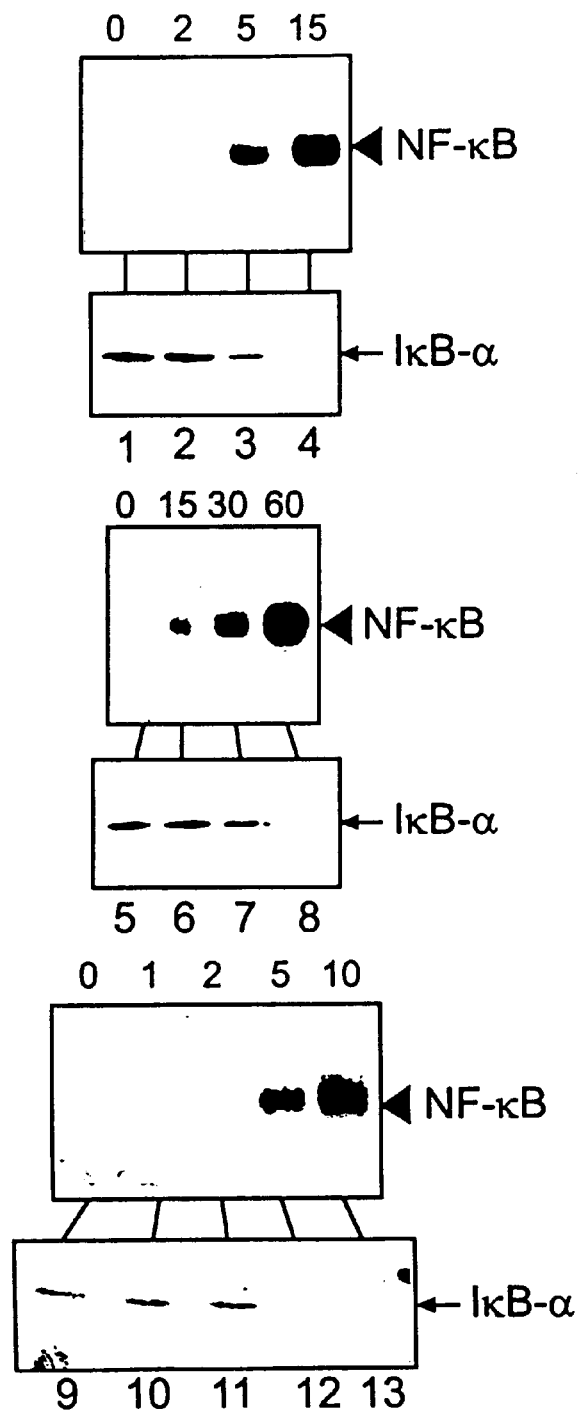
FIG. 2 shows the effect of IL-1β, LPS, and TNF-α on the activation of NF-KB and the stability of IkB-α.

FIG. 2 shows the treatment of 7OZ/3 cells in the upper and middle panel with IL-1β (lanes 2–4) and LPS (lanes 6–8) for the individually stated, different periods (in minutes), followed by a test of the total cell extract with regards to the DNA binding activity of NF-KB and the IkB-α immune reactivity, using EMSA or Western blotting. The lower panel shows the results of the treatment of HeLa cells with TNF-α (lanes 10–13). This figure shows sections of Western blots and sections of fluorograms of native gels. The position of the NF-KB DNA complex in the EMSAs is shown by the filled arrowheads. The position of the IkB-α band on the Western blot is shown by an arrow.

EXAMPLE 3

Effect of a protein synthesis inhibitor on the stability of IkB-α and the activation of NF-KB in 7OZ/3 cells 7OZ/3 cells were treated with 25 μg/ml cycloheximide (Sigma) (as determined by Wall et al., 1986, already at a concentration of 10 μg/ml the protein synthesis is inhibited in 7OZ/3 cells by 90%). Cell culture, extract production, SDS-PAGE and Western blotting was carried out according to example 1. The densitometric test was then carried out by a Howtek Scanmaster 3; the data was evaluated with Quantity One Version 2.2 software.

Figure 3A:
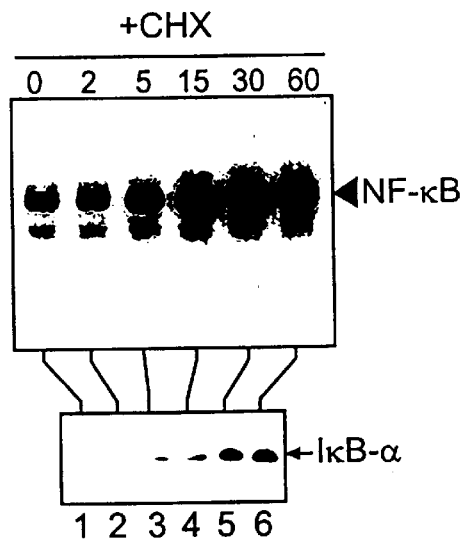
FIG. 3A shows the effect of cycloheximide on the DNA binding of NF-KB and the cellular concentration of IkB-α.
Figure 3B:
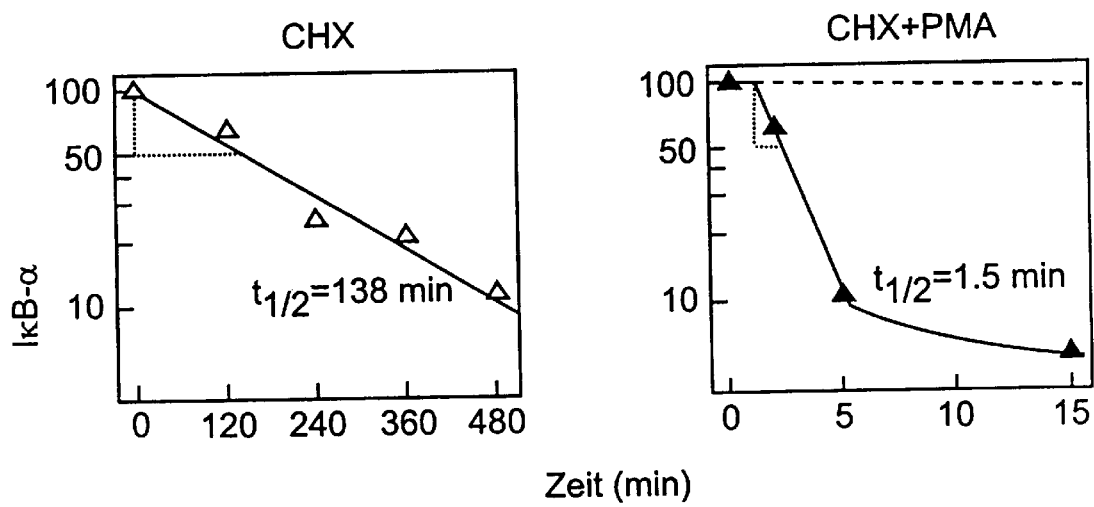
FIG. 3B shows the stability of IkB-α in the absence and presence of PMA.

The result of the experiments is shown in FIG. 3: A: Effect of cycloheximide on the DNA binding of NF-KB and the cellular concentration of IkB-α. The cells were pre-treated with cycloheximide for one hour, followed by a stimulation with PMA for the stipulated period (in minutes). The top panel shows the test of the cell extracts for the DNA binding activity of NF-KB using EMSA, showing a section of the fluorogram of a native gel; the filled arrowhead shows the position of the NF-KB-DNA complex. The lower panel shows the test of the cell extract aliquot on IkB-α using Western blotting; the position of the 38 K IkB-α band is shown by an arrow. B: Stability of IkB-α without and in the presence of PMA. The left panel shows the treatment of cells with only cycloheximide; the right panel shows the treatment of cells with PMA (treatment duration is stipulated in the figure) after a one-hour cycloheximide pre-treatment. (The total cell extracts in high-salt concentrations were produced from cell culture aliquots and identical protein amounts were subjected to SDS-PAGE. The IkB-α concentration was determined by Western blotting and densitometric quantification of the 38 K band in the fluorogram.) The left panel shows the proven IkB-α (in %) at the start of the cycloheximide treatment, the right at the start of the PMA treatment.

EXAMPLE 4

Effect of protease inhibitors on the activation of NF-KB and the stability of IkB-α in 7OZ/3 cells Cell cultures, extract production, SDS-PAGE and Western blotting were carried out according to example 1. The cells were dissolved in 25 μm TPCK or TLCK (both from Sigma), and pre-treated in dimethylsulfoxide (DMSO). The control cultures received an equivalent amount of DMSO.

The results of the experiments are shown in FIG. 4: A: Effect of TPCK on the induction by PMA. The cells were treated without (left panel) or in presence of TPCK with PMA for the stipulated periods. The cell extracts were tested for the DNA binding activity of NF-KB using EMSA (top panel) and for the IkB-α protein quantity using Western blotting (bottom panel). The position of the NF-KB-DNA complex in a section of a fluorogram of a native gel is shown by a filled arrowhead. An arrow shows the position of the 38 K IkB-α band in the Western blot. The weaker lower band is non-specific; its quantity was highly reduced after an affinity-purification of the antibody. B: Effect of TPCK on the activation of NF-KB by IL-1β (I), LPS (L) and PMA (P) in 7OZ/3 cells; in control cells (Co). The cells were treated with TPCK for 10 minutes before stimulation (lanes 6–8) or for an additional 10 minutes after stimulation (lanes 10–12; 30 minutes with IL-1β and PMA or 60 minutes with LPS). The total cell extracts of control cells (lanes 1–4) and cells treated with TPCK (lanes 5–12) were tested for the DNA binding activity of NF-KB using EMSA; a section of a fluorogram of a native gel is shown. The filled arrowhead shows the position of the NF-KB-DNA complex. C: Effect of TLCK on the activation of NF-KB by PMA. 7OZ/3 cells were left untreated (lane 1) or were treated for 10 minutes with either 25 μm TPCK (lane 2) or 25 μm TLCK (lane 3), followed by the addition of PMA. The total cell extracts were tested for DNA binding activity of NF-KB using EMSA. The figure shows a section of the fluorogram; the position of the NF-KB-DNA complex is again shown by a filled arrowhead.

EXAMPLE 5

Effect of PDTC on the activation of NF-KB and the stability of IkB-α in 7OZ/3 cells The cell culture, extract production, EMSA, SDS-PAGE and Western blotting were carried out according to the previous examples. The treatment of the cell cultures with 100 μM ammonium salt of PDTC was implemented as described by Schreck et al. 1992.

Figure 5:
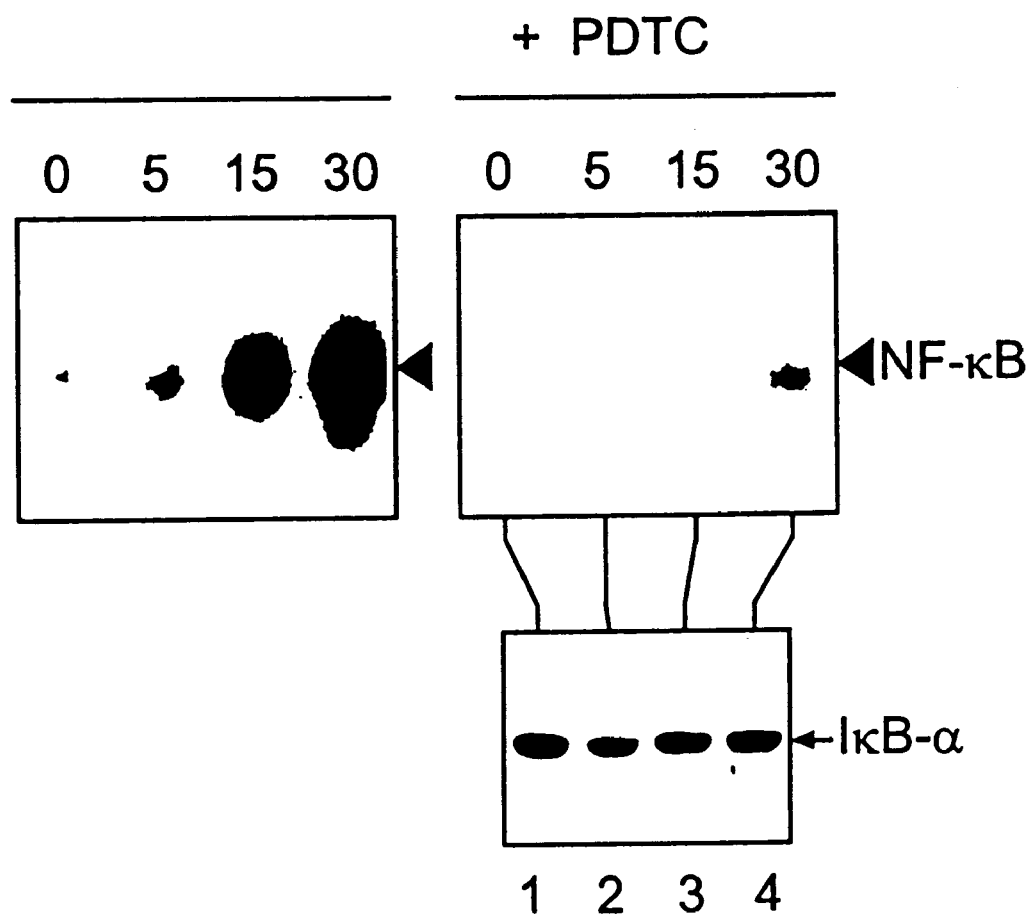
FIG. 5 shows the effect of PDTC on the activation of NF-KB and the stability of IkB-α in 7OZ/3 cells.

The results of the experiments are shown in FIG. 5. The cells were treated during the stipulated times (in minutes) with PMA without (left top panel) or one-hour prior to incubation in the presence of PDTC (right panel). The total cell extracts were tested for DNA binding activity of NF-KB (top panel) using EMSA and IkB-α protein content (bottom panel) using Western blotting, in which, as in the above figures, sections of fluorograms of native gels are shown and the position of the NF-KB-DNA complex is shown by filled arrow heads. A section of a Western blot is shown, in which the position of the 38 K IkB-α band is indicated by an arrow.

EXAMPLE 6

Effect of the protease inhibitor TPCK on the activation of a reporter gene by NF-KB in HeLa cells The cell culture was carried out as in example 1. The cells were transfected by the calcium phosphate method (Wigler et al., 1978). $10^5$ cells per tray were either transfected with 1.5 μg control plasmid, 1.5 μg PUC-TK-Luc or 1.5 μg pUC-KB-TK-Luc. The plasmid pUC19 (ATCC no. 37254, New England Biolabs) was used as a control plasmid. The plasmid pUC TK-Luc contains the sequence coded for luciferase (De Wet et al., 1987) under control of the −105−+52 region of the Herpes simplex thymidine kinase promoter. The plasmid pUC-KB-TK-Luc contains three HIV-LTR fragments of 28 base pairs each, before the TK promoter region, with two KB binding positions each (Nabel et al., 1988). The cells were treated with TPCK (Sigma) 20 minutes before stimulation. The lysis of the cells and the luciferase assay were carried out according to Brasier et al., 1989. The results are shown in relative light units (RLU).

Figure 6:
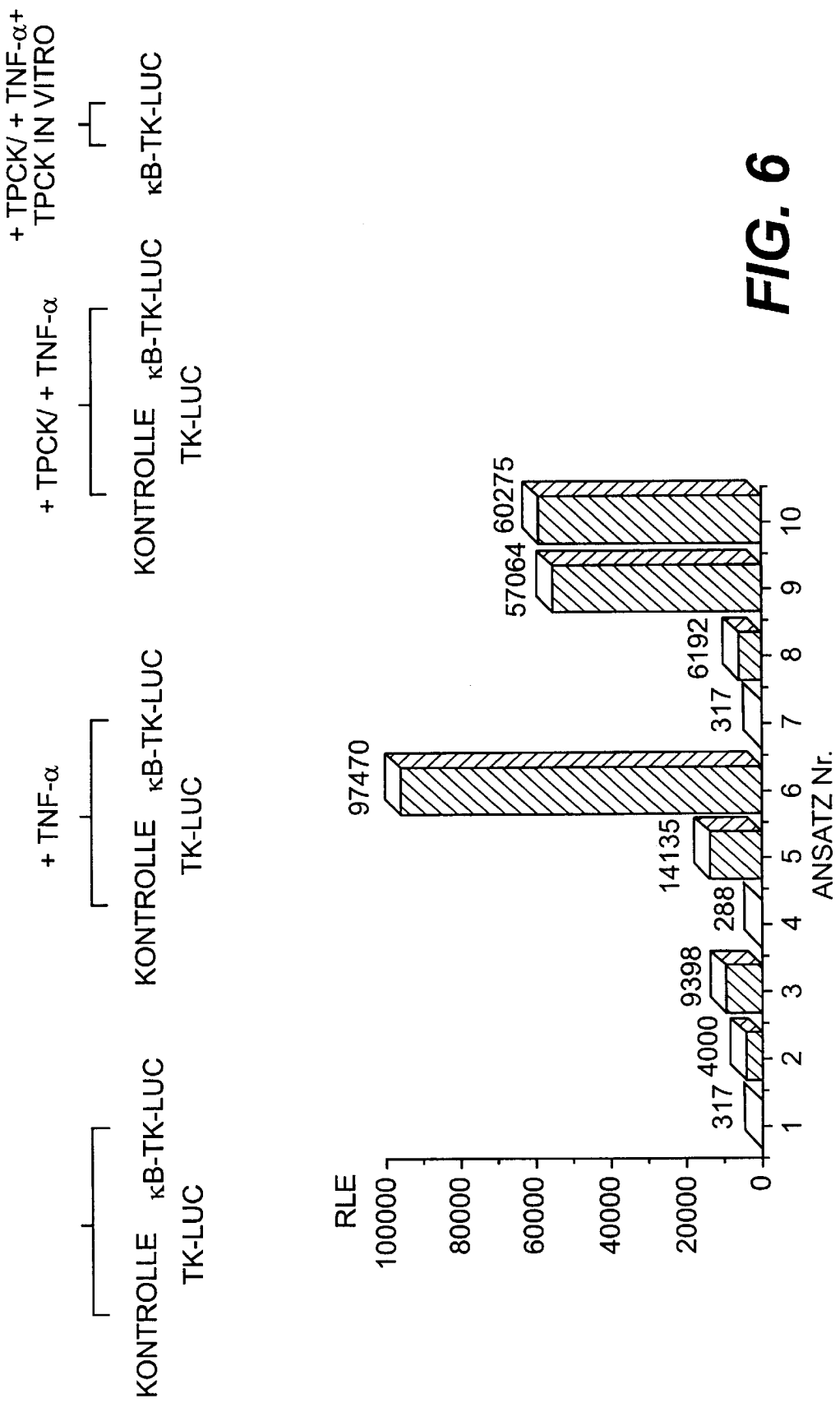
FIG. 6 shows the effect of TPCK on the activation of a reporter gene by NF-KB in HeLa cells.

The results of the experiments carried out are shown in FIG. 6. Formulations 1, 2 and 3 show the basic expression of luciferase in non-stimulated cells. Formulations 4, 5 and 6 show the expression of luciferase after stimulation of the cells with 200 U/ml of human TNF-α for 3 hours. Formulations 7, 8 and 9 show the effect of 25 μM TPCK (in DMSO) on the luciferase expression after TBF-α stimulation. Formulation 10 shows the in vitro effect of TPCK on the luciferase activity. For this purpose 250 μM TPCK (compare formulations 9 and 10) was added to the cell extract.

EXAMPLE 7

Effect of the protease inhibitors Z-Ile-Glu(Ot-Bu)-Ala-leucinal (NBIG) and Z-Leu-leucinal on the activation of NF-KB and the stability of IkB-α in HeLa cells.

Figure 7A:
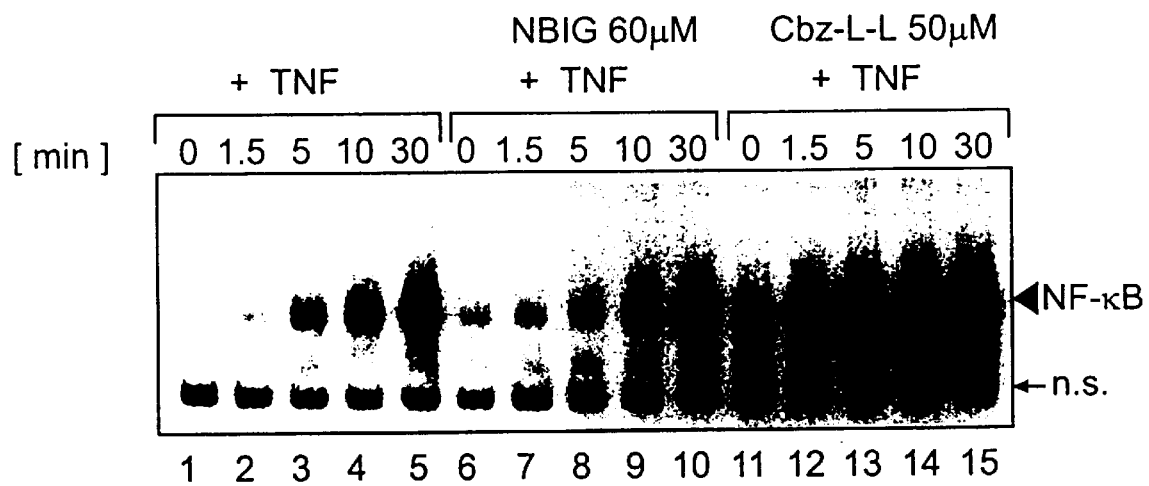
FIG. 7A shows the prevention of the activation of NF-KB after stimulation with TNF-α.
Figure 7B:
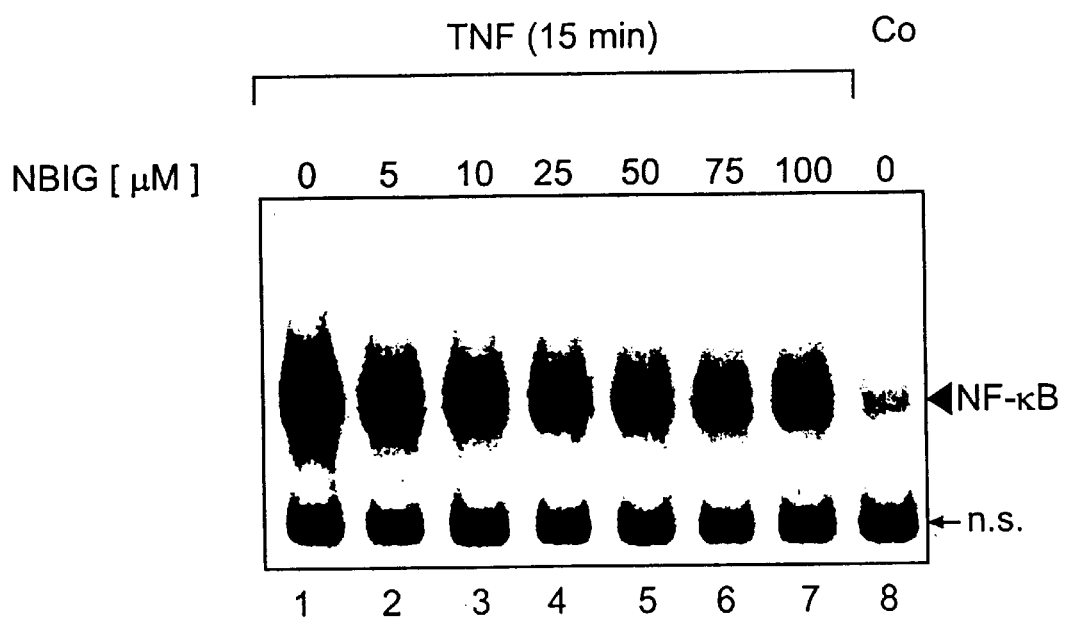
FIG. 7B is a Western blot showing that TNF-α induces the proteolytic degradation of IkB-α.
Figure 8A:
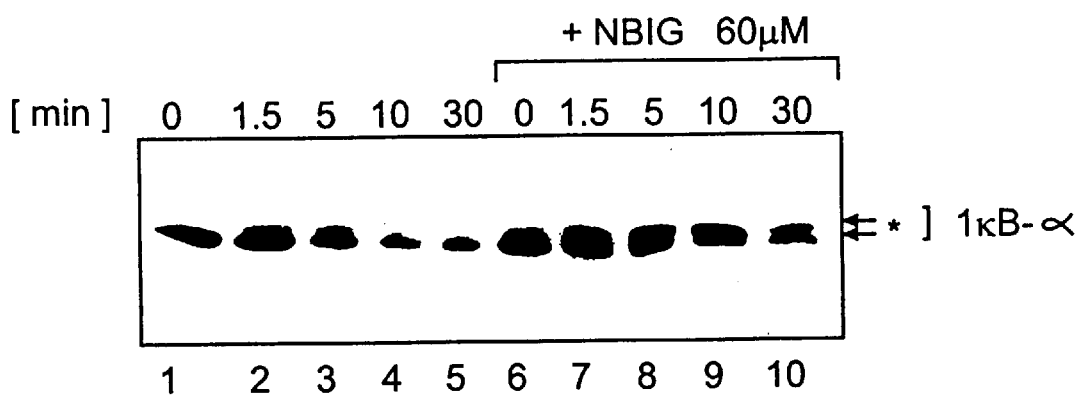
FIG. 8A shows the effect of NBIG on the inhibition of degradation of IkB-α following stimulation with TNF-α.
Figure 8B:
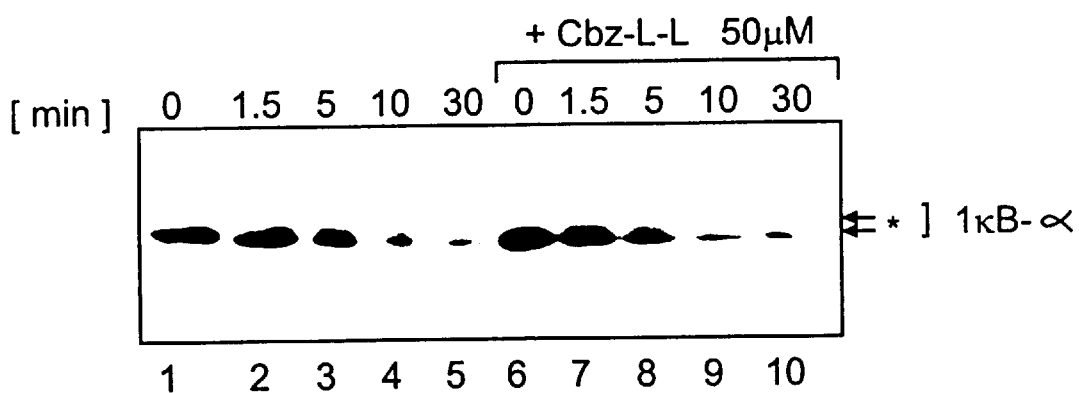
FIG. 8B shows the effect of Cbz-L-L on the inhibition of degradation of IkB-α following stinulation with TNF-α.

The test arrangement in this example corresponded to that of example 4; HeLa cells were cultivated as stated in example 2 and TNF-α was used as inductor for the NF-KB activation. As protease inhibitors Z-Ile-Glu(Ot-Bu)-Ala-leucinal (NBIG) and the chemically related substance Z-Leu-leucinal (Cbz-L-L) were used (Z standing for benzyloxycarbonyl).

a) The electrophoretic mobility shift assays were carried out by using a $^{32}P$ labelled oligonucleotide with a NF-KB binding site on whole cell extracts from HeLa cells. FIG. 7a shows the prevention of the activation of NF-KB after TNF-α stimulation: the comparison after 5 and 10 minutes clearly show that after stimulation with TNF-α in the presence of 60 μM NBIG, considerably less NF-KB-DNA complex is formed than in the control cells (compare lanes 3 and 4 with lanes 8 and 9; "n.s." in FIG. 7 and 8 stands for "non-specific"). With Cbz-L-L this effect did not occur (lanes 11 to 15). The $ID_{50}$ value for NBIG was approx. 50 μM (FIG. 7B).

b) The Western blot analysis showed that TNF-A induces the proteolytic degradation of IkB-α (FIG. 8, lanes 3 to 5). In the presence of 60 μM NBIG, this degradation is greatly reduced. (FIG. 8, compare lanes 4 and 9, 10 minute value). The inhibition of the NF-KB activation after stimulation with TNF-α consequently also creates an inhibition of the degradation of the IkB-α (FIG. 8A). In contrast to the protease inhibitor TPCK (see example 4) the NBIG at a concentration of 60 μm had the special feature of causing an accumulation of a modified form of IkB-α running slower in the SDS gel (FIG. 8a, compare lanes 4 and 9). The inhibitor Cbz-L-L (50 μm) does not show these effects (FIG. 8B). In the figure the slower migrating form of IkB-α is identified with an asterisk.

The incubation of cell fractions with acidic phosphatase from potatoes results in the slower migrating form of IkB-α being transformed back into the faster migrating form. This finding shows that the slower migrating form of IkB-α, which is accumulated after stimulation by TNF-α and under the effect of NBIG, is a phosphorylated form in IkB-α.

In a further experiment NBIG was used together with the phosphate inhibitor okadaic acid (100 nM). The presence of okadaic acid caused the quicker migrating non-phosphorylated form of IkB-α to disappear completely.

Figure 9:
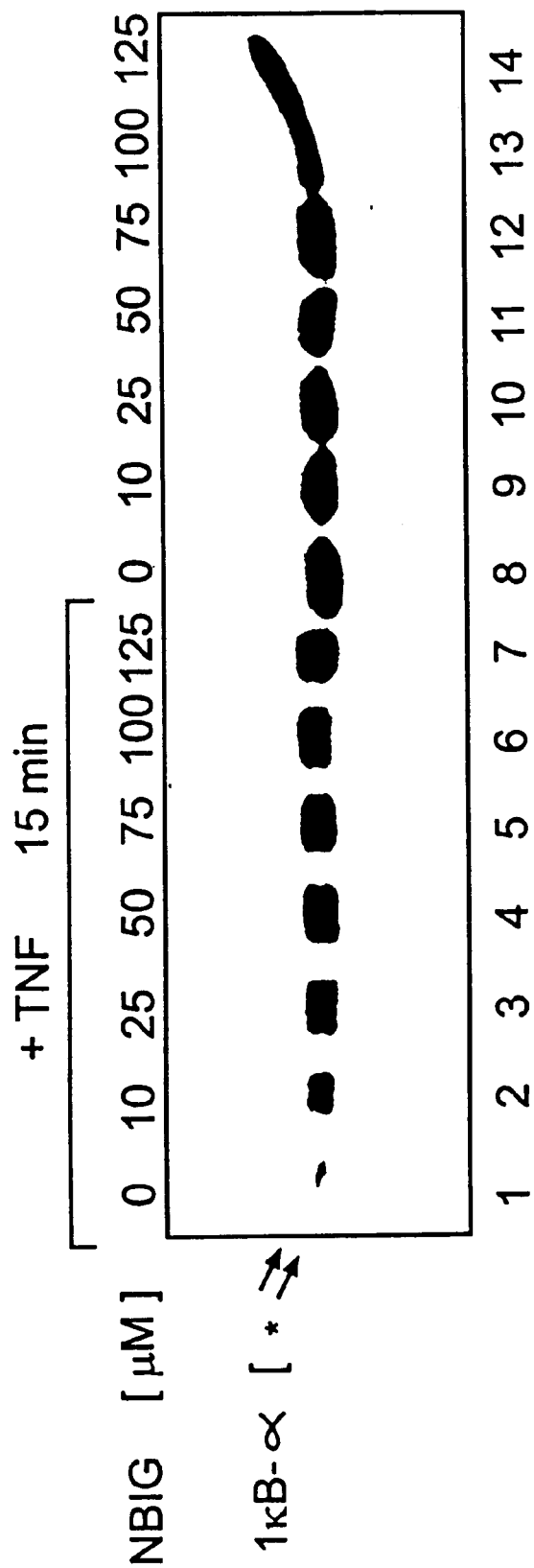
FIG. 9 shows the inability of treatment with NBIG to induce the phosphorylation of IkB-α.

The phosphorylation of IkB-α is not induced by treatment with NBIG (FIG. 9, lanes 8 to 14), not even at a concentration of 125 AM (lane 14). The phosphorylated form of IkB-α is thus only created when the cells are induced with TNF-A (FIG. 9, lanes 2 to 7), the quantity of modified IkB-α rising with the concentration of NBIG. The observation that the occurrence and the stabilisation of the phosphorylated form in IkB-α is not simultaneous with the activation of NF-KB (compare FIG. 8A, lanes 6 to 9 with FIG. 7A, lanes 6 to 9), reinforces the assumption, that phosphorylation of IkB-α in intact cells is insufficient for an activation of NF-KB.

EXAMPLE 8

Inhibition of the expression of NF-KB regulated cytokine IL-6 and IL-8 in HeLa cells by the protease inhibitor NBIG The principle of the test arrangement corresponded to that of the previous examples.

The cells were stimulated—with or without 30 minutes of pre-treatment with 100 μmol NBIG—with TNF (200 E/ml) or with PMA (50 ng/ml) and the concentration of IL-6 or IL-8 was measured in the cell supernatant at various intervals using ELISA (British Biotechnology Products Ltd.). The expression values are listed in the table. The values show that after 120 minutes of stimulation in the presence of the protease inhibitors, the production of IL-6 is inhibited by 79% or 73% (TNF stimulation) and the production of IL-8 is inhibited by 90% or 98% (PMA stimulation).

TABLE

|  | IL-6 (pg/ml) | | | IL-8 (pg/ml) | | |
| --- | --- | --- | --- | --- | --- | --- |
|  | 0' | 15' | 120' | 0' | 15' | 120' |
| TNF | — | 875 | 6750 | — | — | 52 |
| TNF + NBIG | — | 875 | 1438 | — | — | 5 |

TABLE-continued

|  | IL-6 (pg/ml) | | | IL-8 (pg/ml) | | |
| --- | --- | --- | --- | --- | --- | --- |
|  | 0' | 15' | 120' | 0' | 15' | 120' |
| PMA | — | 750 | 12813 | — | — | 410 |
| PMA + NBIG | — | 1125 | 3438 | — | — | 10 |

REFERENCES

Baeuerle, P. A. and Baltimore, D., 1988a, Cell 53, 211–217.
Baeuerle, P. A. and Baltimore, D., 1988b, Science 242, 540–546.
Baeuerle, P. A., 1991, Biochim. Biophys. Acta 1072, 63–80.
Baeuerle, P. A. and Baltimore, D., 1991, In: Molecular Aspects of Cellular Regulation Vol. 6, Hormonal Control Regulation of Gene Transcription, Cohen, P. and Foulkes, J. G. (eds.), Elsevier/North Holland Biomedical Press, Amsterdam, pp. 409–432.
Blank, V., Kourilsky, P. and Israel, A., 1992, Trends Biochem. Sci. 17, 135–140.
Bomsztyk, K. et al., 1991, Cell. Regul. 2, 329–337.
Brasier, A. R., Tate, J. E. and Habener, J. F., 1989, BioTechniques 7, 1116–1122.
De Wet, J. R., Wood, K., DeLuca. M. Helsinki, 13. and Subramani, S., 1987, Mol. Cell. Biol. 7, 725–737.
Gosh, S. and Baltimore, D, 1990, Nature 344, 678–682.
Grimm, S. and Baeuerle, P. A., 1993, Biochem. J. 290, 297–308.
Gritz, L. and Davies, J., 1983, Gene 25, 179–188.
Hartmann, A., 1991, BioTec 5, 40–45.
Haskill et al., 1991, Cell 65, 1281–1289.
Henkel et al., 1992, Cell 68, 1121–1133.
Hochstrasser, M. and Varshavsky, A., 1990, Cell 61, 697–708.
Kerr et al., 1991, Genes Dev. 5, 1464–1476.
Kricka, L. Ji, 1988, Analyt. Biochem. 175, 14–21.
Laemmli, U. K., 1970, Nature 227, 680–685.
Meichle, A., Schütze, S., Hensel, G., Brunsing, D. and Krönke, M., 1990, J. Biol. Chem. 265,8339–8347.
Mulligan, R. and Berg, P., 1981, Proc.Natl.Acad.Sci. USA 78, 2072–2076.
Nabel et al., 1988, Science 239, 1299–1301.
Nolan, G. P. and Baltimore, D., 1992, Curr. Opin. Genet. Dev. 2, 211–220.
Orlowski, M., 1990, Biochemistry 29, 10289–10297.
Remington's Pharmaceutical Sciences, 1980, Mack Publ. Co., Easton, Pa, Osol (ed.).
Rivett, A. J., 1989, Arch. Biochem. Biophys. 268, 1–8.
Schreck, R., Rieber, P. and Baeuerle, P. A., 1991, EMBO J. 10, 2247–2258.
Schreck, R., Albermann, K. and Baeuerle, P. A., 1992a, Free Rad. Res. Comms. 17, 221–237.
Schreck, R., Meier, B., Mannel, D., Dröge, W. and Baeuerle, P. A., 1992b, J. Exp. Med. 175, 1181–1194.
Shirakawa, F. and Mizel, S., 1989, Mol. Cell. Biol. 9, 2424–2430.

Sen, R. and Baltimore, D., 1986, Cell 47, 921–928
Southern, P. and Berg, P., 1982, J. Mol. Appl. Gen, 1, 327.
Subramani, S. and DeLuca, M., 1987, Genetic Engineering, Principles and Methods, J. K. Sedlow ed., Plenum Press, New York, Band 10, 75–89.
Tanahashi, H., Ito, T., Inouye, S., Tsuji, F. I. and Sakaki, Y., 1990, Gene 96, 249–255.
Wall, R. et al., 1986, Proc.Natl.Acad.Sci. USA 83, 295–298.
Wieland, E. et al., 1985, Arztl. Lab. 31, 203–214.
Wigler et al., 1978, Cell 14, 725–731.
Zabel, U., Henkel, T., dos Santos Silva, M. and Baeuerle, P. A., 1993, EMBO J. 12, 201–211.

What is claimed is:

1. A process for inhibiting the transcription of genes in higher eukaryotic cells by inhibiting the activity of NF-KB, comprising treating the cells with a substance which specifically inhibits the proteolytic degradation of IkB-α.

2. A process for identifying a substance that inhibits NF-KB activation, comprising testing a substance for its ability to specifically inhibit the proteolytic degradation of IkB-α, by exposing an IkB-α containing substrate, in the presence of a test substance, to a preparation that shows proteolytic activity for IkB-α in the absence of the test substance, and determining whether the test substance specifically inhibits the proteolytic degradation of IkB-α.

3. The process according to claim 2, wherein the exposing step includes using an extract of cells, which were treated with an inducer for the NF-KB activation, or a fraction of said extract.

4. The process according to claim 2, wherein a cell-free system is used for the exposing step.

5. The process according to claim 4, wherein recombinant IkB-α bound to a fixed carrier is used as the substrate containing IkB-α in the exposing step.

6. The process according to claim 4, wherein recombinant IkB-α in a solution is used as the substrate containing IkB-α in the exposing step.

7. The process according to claim 4, wherein phosphorylated IkB-α is used as the substrate containing IkB-α in the exposing step.

8. The process according to claim 7, wherein phosphorylated IkB-α is used, which was obtained from the treatment of cells with a substance inducing NF-KB activation and with a substance specifically which inhibits the proteolytic degradation of IkB-α and effects the accumulation of the phosphorylated form of IkB-α.

9. The process according to claim 2, further comprising inducing NF-KB activation in higher eukaryotic cells, which have been transformed with a reporter gene construct that responds to NF-KB activation, in the presence of the test substance, and measuring expression of the reporter gene construct.

10. The process according to claim 9, wherein the exposing of the IkB-α substrate and the inducing of NF-KB activation are performed in parallel.

11. The process according to claim 9, wherein the inducing of NF-KB activation is performed after the exposing of the IkB-α substrate.

12. The process according to claim 9, wherein said exposing step is performed in a cell-free system, recombinant IkB-α is used as said substrate, said step of inducing NF-KB activation includes exposing to a test substance luciferase-gene-transformed human cells that are stimulated with an inducer for NF-KB activation, and measuring luciferase expression.

13. The process according to claim 12, wherein the luciferase gene construct contains at least two KB motifs.

14. A substance that specifically inhibits the proteolytic degradation of IkB-α which is used for the treatment of pathological conditions, which involve the expression of genes which are controlled by the transcription factor NF-KB.

15. A pharmaceutical composition comprising at least one substance that specifically inhibits the proteolytic degradation of IkB-α, and a pharmaceutically acceptable carrier.

16. A method for the treatment of pathological conditions, which involve the expression of genes which are controlled by the transcription factor NF-KB, comprising administering to a patient a substance that specifically inhibits the proteolytic degradation of IkB-α.

* * * * *

UNITED STATES PATENT AND TRADEMARK OFFICE
CERTIFICATE OF CORRECTION

PATENT NO. : 6,090,542
DATED : July 18, 2000
INVENTOR(S) : Bacuerle *et al.*

It is certified that error appears in the above-identified patent and that said Letters Patent is hereby corrected as shown below:

Title page, item [75], lines 2-3, "Thomas Henkel, San Francisco, Calif." should read --Thomas Henkel, Munich, Germany--;

Claim 8, col. 20, line 48, "substance specifically which" should read --substance which specifically--; and Claim 16, col. 22, line 5, "method" should read --process--.

Signed and Sealed this

Seventeenth Day of April, 2001

*Attest:*

NICHOLAS P. GODICI

*Attesting Officer*   *Acting Director of the United States Patent and Trademark Office*